US012616452B2

(12) United States Patent

Takayama

(10) Patent No.: US 12,616,452 B2

(45) Date of Patent: May 5, 2026

(54) ULTRASOUND DIAGNOSTIC SYSTEM AND CONTROL METHOD OF ULTRASOUND DIAGNOSTIC SYSTEM

(71) Applicant: FUJIFILM Corporation, Tokyo (JP)

(72) Inventor: Hidetoshi Takayama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

(21) Appl. No.: 18/583,808

(22) Filed: Feb. 21, 2024

(65) Prior Publication Data

US 2024/0325000 A1 Oct. 3, 2024

(30) Foreign Application Priority Data

Mar. 27, 2023 (JP) ................................. 2023-050212

(51) Int. Cl.
*A61B 8/00* (2006.01)

(52) U.S. Cl.
CPC .............. *A61B 8/54* (2013.01); *A61B 8/4472* (2013.01); *A61B 8/4477* (2013.01); *A61B 8/463* (2013.01)

(58) Field of Classification Search
CPC ....... A61B 8/54; A61B 8/4472; A61B 8/4477; A61B 8/463; A61B 8/4245; A61B 8/461; A61B 8/565; A61B 8/4427
See application file for complete search history.

(56) References Cited

U.S. PATENT DOCUMENTS

2015/0005630 A1* 1/2015 Jung ...................... A61B 8/465
600/437
2019/0357881 A1* 11/2019 Choi ..................... A61B 8/4263

(Continued)

FOREIGN PATENT DOCUMENTS

JP 2018-014076 A 1/2018
JP 2022-545355 A 10/2022

*Primary Examiner* — Michael J Carey
*Assistant Examiner* — Zainab Mohammed Aldarraji
(74) *Attorney, Agent, or Firm* — Studebaker Brackett PLLC

(57) ABSTRACT

Provided are an ultrasound diagnostic system and a control method of an ultrasound diagnostic system capable of performing proper diagnoses on a plurality of subjects at once by using a single diagnostic apparatus.

There is provided an ultrasound diagnostic system including: a plurality of image acquisition apparatuses each having an ultrasound probe and a portable terminal; a diagnostic apparatus wirelessly connected to the plurality of image acquisition apparatuses; and a diagnostic apparatus side monitor, in which the plurality of image acquisition apparatuses each wirelessly transmit an ultrasound image acquired by using the ultrasound probe to the diagnostic apparatus in association with position information of the ultrasound probe acquired by a position information acquisition module of the ultrasound probe, the diagnostic apparatus displays a plurality of ultrasound images of a plurality of subjects on one screen of the diagnostic apparatus side monitor, and the diagnostic apparatus displays a plurality of identification marks corresponding to a plurality of pieces of the position information associated with the ultrasound images of the plurality of subjects on the diagnostic apparatus side monitor in correspondence with the plurality of ultrasound images.

20 Claims, 9 Drawing Sheets

(56)  References Cited

U.S. PATENT DOCUMENTS

2019/0383920  A1*  12/2019  Kook .................. G01S 7/52053
2021/0059758  A1     3/2021  Avendi et al.
2022/0047248  A1*   2/2022  Osumi .................. A61B 8/465

* cited by examiner

ULTRASOUND DIAGNOSTIC SYSTEM AND CONTROL METHOD OF ULTRASOUND DIAGNOSTIC SYSTEM

CROSS-REFERENCE TO RELATED APPLICATIONS

The present application claims priority under 35 U.S.C. § 119 to Japanese Patent Application No. 2023-050212, filed on Mar. 27, 2023. The above application is hereby expressly incorporated by reference, in its entirety, into the present application.

BACKGROUND OF THE INVENTION

1. Field of the Invention

The present invention relates to an ultrasound diagnostic system and a control method of an ultrasound diagnostic system for performing diagnoses on a plurality of subjects at once by using a single diagnostic apparatus.

2. Description of the Related Art

Hitherto, in the medical field, an ultrasound diagnostic apparatus using ultrasound images has been put into practical use. The ultrasound diagnostic apparatus typically comprises an ultrasound probe incorporating a transducer array, and an apparatus body connected to the ultrasound probe, and transmits an ultrasound beam from the ultrasound probe toward a subject, receives an ultrasound echo from the subject through the ultrasound probe, and electrically processes a reception signal thereof to generate an ultrasound image.

In addition, as disclosed in JP2022-545355A and JP2018-014076A, a portable ultrasound diagnostic apparatus that establishes a wireless connection between an ultrasound probe and an apparatus body through wireless communication has been developed to improve operability and mobility of the ultrasound probe. The ultrasound image acquired by the ultrasound probe is displayed on a monitor of the apparatus body.

Such a wireless ultrasound probe, which is excellent in operability and mobility, is particularly useful in, for example, situations where emergency rescue is required.

SUMMARY OF THE INVENTION

However, only displaying ultrasound images acquired from individual subjects on the monitor makes it difficult to quickly advance the diagnosis in a case in which it is desirable to diagnose a plurality of subjects at once by using a single diagnostic apparatus, for example, in situations such as disasters or traffic accidents.

Even in a case in which a plurality of ultrasound images respectively acquired from the plurality of subjects are simultaneously displayed on one screen of the monitor, which ultrasound image is acquired from which subject should be accurately specified; otherwise, there is a concern about performing incorrect diagnosis.

The present invention has been made in order to solve such a conventional problem, and an object of the present invention is to provide an ultrasound diagnostic system and a control method of an ultrasound diagnostic system capable of performing proper diagnoses on a plurality of subjects at once by using a single diagnostic apparatus.

According to the following configuration, the above-described object can be achieved.

[1] An ultrasound diagnostic system comprising:
a plurality of image acquisition apparatuses each having an ultrasound probe and a portable terminal that displays an ultrasound image acquired by using the ultrasound probe;
a diagnostic apparatus wirelessly connected to the plurality of image acquisition apparatuses; and
a diagnostic apparatus side monitor connected to the diagnostic apparatus,
in which the ultrasound probes of the plurality of image acquisition apparatuses each include a position information acquisition module that acquires position information of the ultrasound probe,
the plurality of image acquisition apparatuses each wirelessly transmit the ultrasound image acquired by using the ultrasound probe to the diagnostic apparatus in association with the position information of the ultrasound probe acquired by the position information acquisition module,
the diagnostic apparatus displays ultrasound images of a plurality of subjects acquired by the plurality of image acquisition apparatuses on one screen of the diagnostic apparatus side monitor, and
the diagnostic apparatus displays a plurality of identification marks corresponding to a plurality of pieces of the position information associated with the ultrasound images of the plurality of subjects on the diagnostic apparatus side monitor in correspondence with the ultrasound images of the plurality of subjects.

[2] The ultrasound diagnostic system according to [1],
in which the diagnostic apparatus has an identification mark generation unit that generates the plurality of identification marks.

[3] The ultrasound diagnostic system according to [1] or [2],
in which the position information acquisition module is an azimuthal angle detection module that detects an azimuthal angle of the ultrasound probe with respect to the diagnostic apparatus as the position information.

[4] The ultrasound diagnostic system according to [3],
in which the identification mark is a mark representing a direction from the diagnostic apparatus toward the ultrasound probe based on the azimuthal angle detected as the position information.

[5] The ultrasound diagnostic system according to [1] or [2],
in which the ultrasound probe of the image acquisition apparatus has a light emitting unit that selectively emits rays of light of a plurality of colors, and the identification mark has a color corresponding to the color of the light emitted from the light emitting unit.

[6] The ultrasound diagnostic system according to [1] or [2],
in which the ultrasound probe of the image acquisition apparatus has a probe side monitor that displays a probe side mark, and the identification mark has a shape corresponding to the probe side mark.

[7] The ultrasound diagnostic system according to any one of [1] to [6],
in which the image acquisition apparatus has a notification unit provided in at least one of the ultrasound probe or the portable terminal, and in a case in which any of the ultrasound images of the plurality of subjects displayed on the diagnostic apparatus side monitor is designated by a user, a notification is made by the notification unit of the image acquisition apparatus having the ultrasound probe corresponding to the position information associated with the designated ultrasound image.

[8] The ultrasound diagnostic system according to [7], in which the notification unit issues the notification by using at least one of sound, vibration, or light.

[9] The ultrasound diagnostic system according to any one of [1] to [8], in which the ultrasound probe of the image acquisition apparatus is wirelessly connected to the diagnostic apparatus.

[10] The ultrasound diagnostic system according to any one of [1] to [8], in which the portable terminal of the image acquisition apparatus is wirelessly connected to the diagnostic apparatus.

[11] A control method of an ultrasound diagnostic system, comprising:

acquiring, in a plurality of image acquisition apparatuses each having an ultrasound probe and a portable terminal that displays an ultrasound image acquired by using the ultrasound probe, position information of the ultrasound probe;

wirelessly transmitting the ultrasound image acquired by using the ultrasound probe in the plurality of image acquisition apparatuses to a diagnostic apparatus in association with the position information of the ultrasound probe;

displaying ultrasound images of a plurality of subjects acquired by the plurality of image acquisition apparatuses on one screen of a diagnostic apparatus side monitor; and displaying a plurality of identification marks corresponding to a plurality of pieces of the position information associated with the ultrasound images of the plurality of subjects on the diagnostic apparatus side monitor in correspondence with the ultrasound images of the plurality of subjects.

In the ultrasound diagnostic system according to the present invention, the ultrasound probes of the plurality of image acquisition apparatuses each include a position information acquisition module that acquires position information of the ultrasound probe, the plurality of image acquisition apparatuses each wirelessly transmit the ultrasound image acquired by using the ultrasound probe to the diagnostic apparatus in association with the position information of the ultrasound probe acquired by the position information acquisition module, the diagnostic apparatus displays ultrasound images of a plurality of subjects acquired by the plurality of image acquisition apparatuses on one screen of the diagnostic apparatus side monitor, and the diagnostic apparatus displays a plurality of identification marks corresponding to a plurality of pieces of the position information associated with the ultrasound images of the plurality of subjects on the diagnostic apparatus side monitor in correspondence with the ultrasound images of the plurality of subjects. Therefore, it is possible to perform proper diagnoses on the plurality of subjects at once by using a single diagnostic apparatus.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value.

In the present specification, "same" and "identical" include error ranges generally allowed in the technical field.

Embodiment 1

Figure 1:
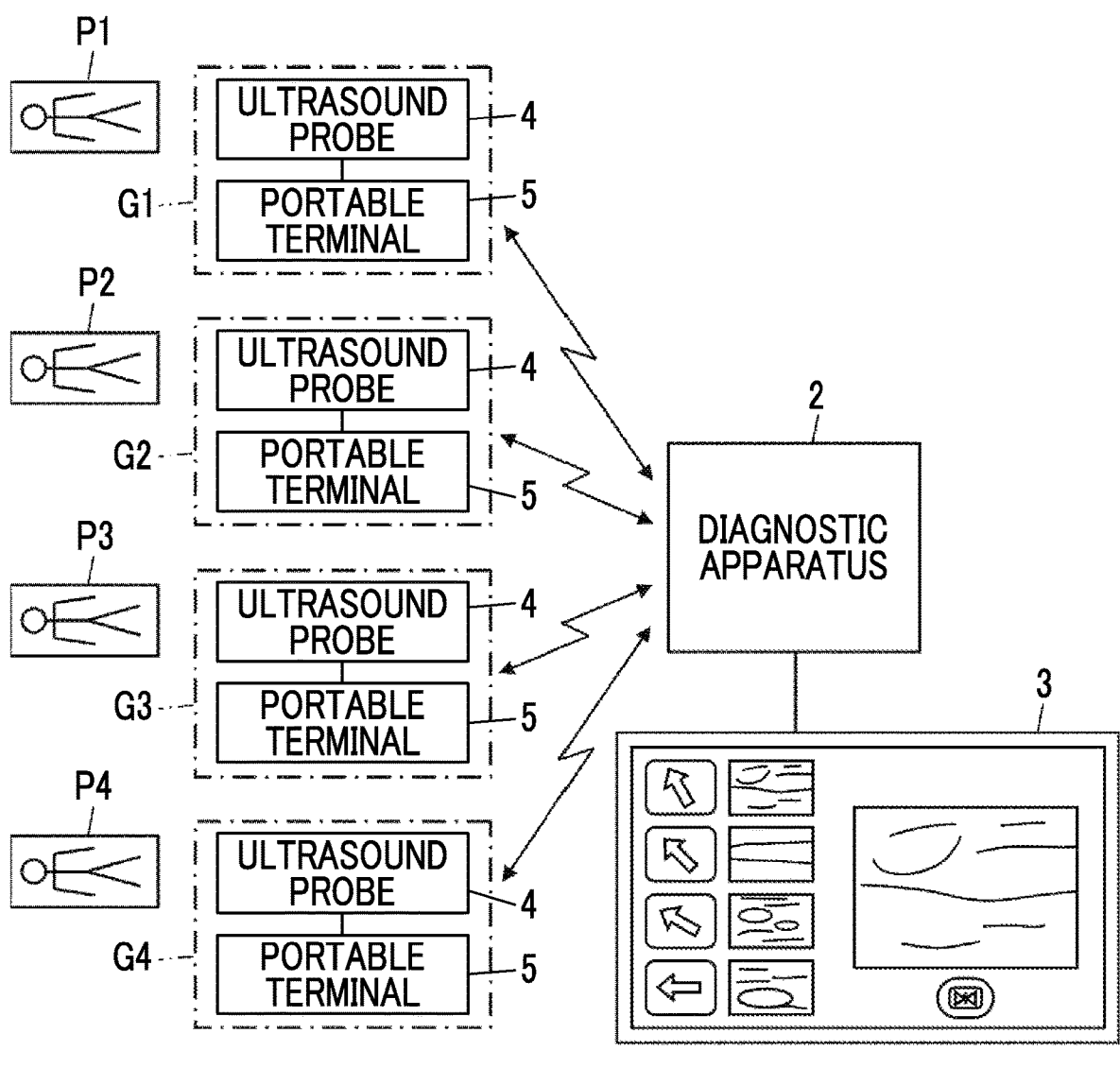
FIG. 1 is a block diagram showing a configuration of an ultrasound diagnostic system according to Embodiment 1 of the present invention.

FIG. 1 shows a configuration of an ultrasound diagnostic system according to Embodiment 1 of the present invention. The ultrasound diagnostic system comprises a plurality of image acquisition apparatuses G1 to G4, a diagnostic apparatus 2, and a diagnostic apparatus side monitor 3. The plurality of image acquisition apparatuses G1 to G4 are disposed in the vicinity of a plurality of subjects P1 to P4 to correspond to the subjects P1 to P4, and each have an ultrasound probe 4 and a portable terminal 5 wirelessly connected to the ultrasound probe 4. The diagnostic apparatus 2 is wirelessly connected to the plurality of image acquisition apparatuses G1 to G4, and the diagnostic apparatus side monitor 3 is connected to the diagnostic apparatus 2.

For example, the diagnostic apparatus 2 is operated by a user such as a doctor, and the plurality of image acquisition apparatuses G1 to G4, for which operations are divided among operators such as a plurality of ultrasound technicians or nurses, can be operated by the operators.

Figure 2:
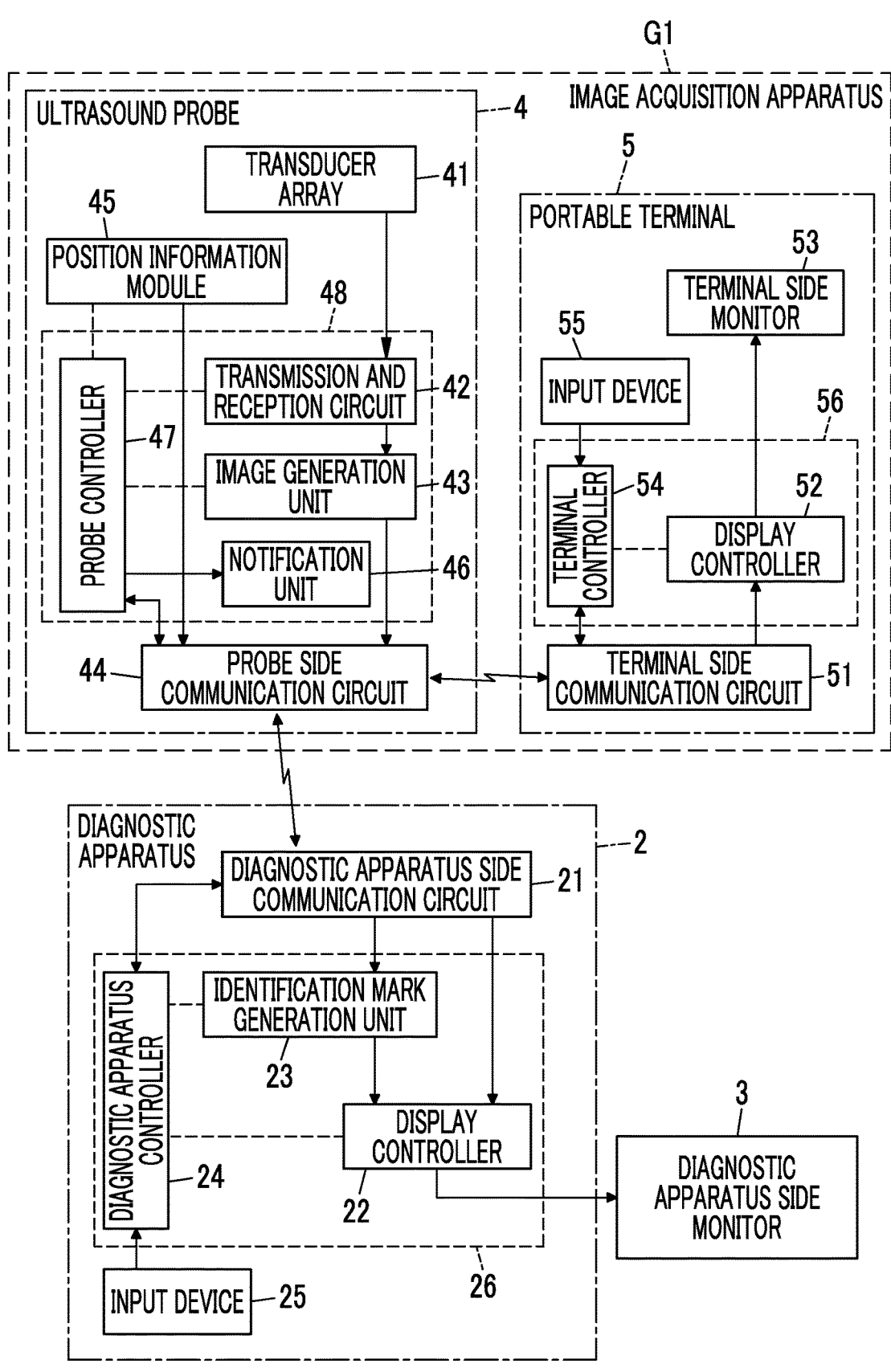
FIG. 2 is a block diagram showing internal configurations of each image acquisition apparatus and a diagnostic apparatus of the ultrasound diagnostic system according to Embodiment 1 of the present invention.

FIG. 2 shows internal configurations of the ultrasound probe 4 and the portable terminal 5 of the image acquisition apparatus G1 and an internal configuration of the diagnostic apparatus 2.

The ultrasound probe 4 has a transducer array 41, and a transmission and reception circuit 42, an image generation unit 43, and a probe side communication circuit 44 are sequentially connected to the transducer array 41. In addition, the ultrasound probe 4 has a position information module 45 and a notification unit 46, and a probe controller 47 is connected to the transmission and reception circuit 42, the image generation unit 43, the probe side communication circuit 44, the position information module 45, and the notification unit 46.

Further, a probe side processor 48 is composed of the transmission and reception circuit 42, the image generation unit 43, the notification unit 46, and the probe controller 47.

Meanwhile, the portable terminal 5 has a terminal side communication circuit 51, and a display controller 52 and a terminal side monitor 53 are sequentially connected to the terminal side communication circuit 51. A terminal controller 54 is connected to the terminal side communication circuit 51 and the display controller 52, and an input device 55 is further connected to the terminal controller 54.

A terminal side processor 56 is composed of the display controller 52 and the terminal controller 54.

Although not shown, the ultrasound probe 4 and the portable terminal 5 in each of the image acquisition apparatuses G2 to G4 also have the same configurations as those of the ultrasound probe 4 and the portable terminal 5 of the image acquisition apparatus G1 shown in FIG. 2.

The diagnostic apparatus 2 has a diagnostic apparatus side communication circuit 21, and a display controller 22 and an identification mark generation unit 23 are connected to the diagnostic apparatus side communication circuit 21. A diagnostic apparatus controller 24 is connected to the diagnostic apparatus side communication circuit 21, the display controller 22, and the identification mark generation unit 23, and an input device 25 is further connected to the diagnostic apparatus controller 24.

A diagnostic apparatus side processor 26 is composed of the display controller 22, the identification mark generation unit 23, and the diagnostic apparatus controller 24.

Further, the diagnostic apparatus side monitor 3 is connected to the display controller 22 of the diagnostic apparatus 2.

The transducer array 41 of the ultrasound probe 4 has a plurality of ultrasound transducers that are one-dimensionally or two-dimensionally arranged. These ultrasound transducers each transmit an ultrasound wave in accordance with a drive signal supplied from the transmission and reception circuit 42 and receive an ultrasound echo from the subject to output a signal based on the ultrasound echo. For example, each ultrasound transducer includes a piezoelectric body and electrodes formed at both ends of the piezoelectric body. The piezoelectric body consists of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like.

Figure 3:
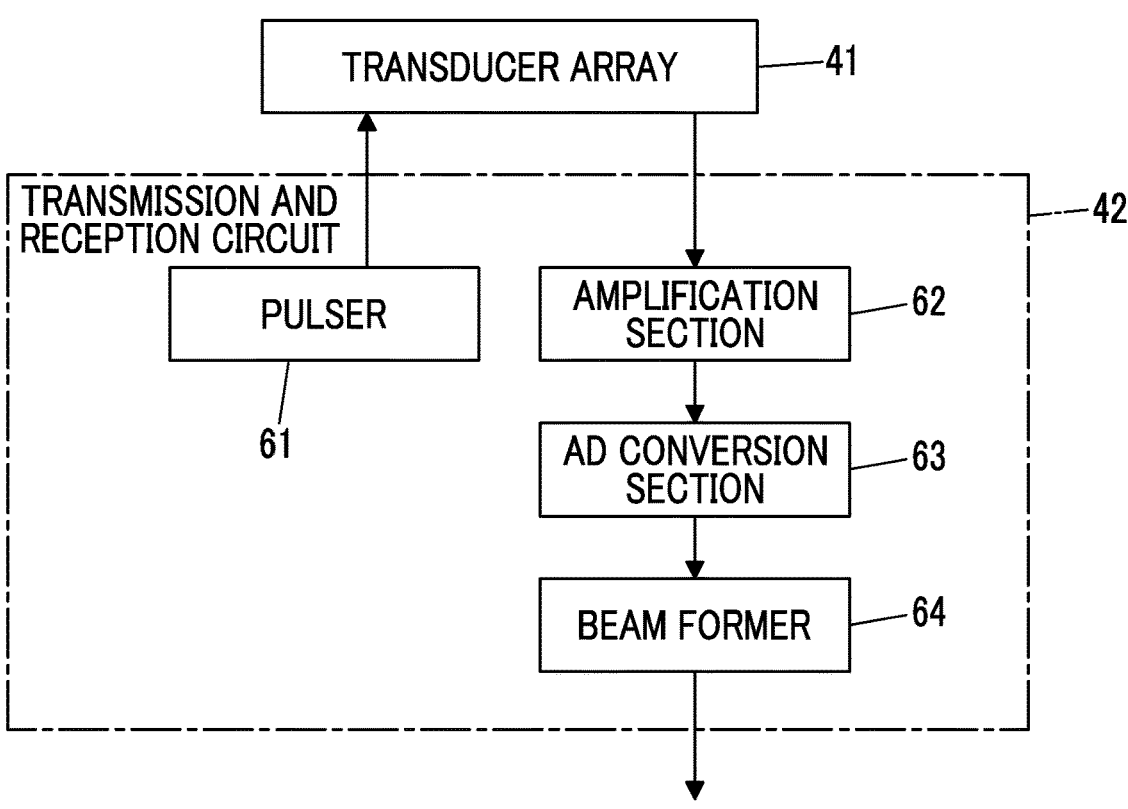
FIG. 3 is a block diagram showing an internal configuration of a transmission and reception circuit in Embodiment 1 of the present invention.

The transmission and reception circuit 42 transmits the ultrasound wave from the transducer array 41 and generates a sound ray signal based on a reception signal acquired by the transducer array 41, under the control of the probe controller 47. As shown in FIG. 3, the transmission and reception circuit 42 has a pulsar 61 connected to the transducer array 41, and an amplification section 62, an analog-to-digital (AD) conversion section 63, and a beam former 64 that are sequentially connected in series to the transducer array 41.

The pulsar 61 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 41 form an ultrasound beam based on a transmission delay pattern selected according to a control signal from the probe controller 47. In this way, in a case in which a pulsed or continuous wave-like voltage is applied to the electrodes of the ultrasound transducer of the transducer array 41, the piezoelectric body expands and contracts to generate a pulsed or continuous wave-like ultrasound wave from each of the ultrasound transducers, thereby forming an ultrasound beam from the combined wave of these ultrasound waves.

The transmitted ultrasound beam is reflected in, for example, a target such as a site of the subject and propagates toward the transducer array 41 of the ultrasound probe 4. The ultrasound echo propagating toward the transducer array 41 in this way is received by each of the ultrasound transducers constituting the transducer array 41. In this case, each of the ultrasound transducers constituting the transducer array 41 receives the propagating ultrasound echo to expand and contract to generate a reception signal, which is an electrical signal, and outputs these reception signals to the amplification section 62.

The amplification section 62 amplifies the signal input from each of the ultrasound transducers constituting the transducer array 41 and transmits the amplified signal to the AD conversion section 63. The AD conversion section 63 converts the signal transmitted from the amplification section 62 into digital reception data. The beam former 64 performs so-called reception focus processing by applying and adding a delay to each reception data received from the AD conversion section 63. Through the reception focus processing, the sound ray signal in which each reception data converted by the AD conversion section 63 is phase-summed and a focus of the ultrasound echo is narrowed down is acquired.

Figure 4:
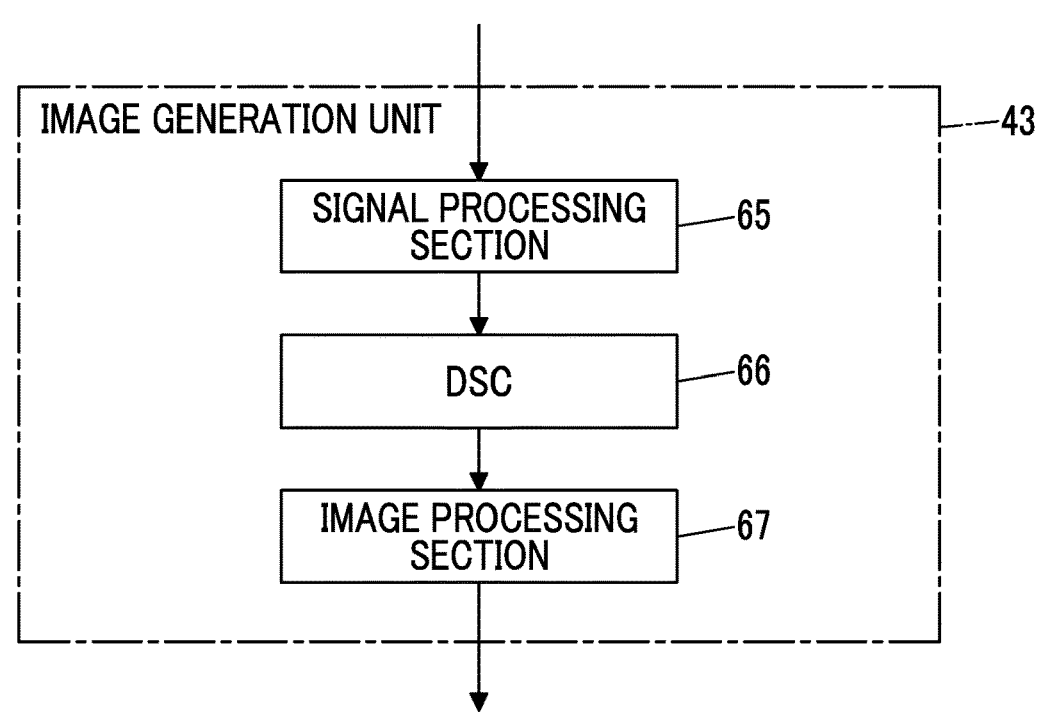
FIG. 4 is a block diagram showing an internal configuration of an image generation unit in Embodiment 1 of the present invention.

As shown in FIG. 4, the image generation unit 43 has a configuration in which a signal processing section 65, a digital scan converter (DSC) 66, and an image processing section 67 are sequentially connected in series.

The signal processing section 65 generates a B-mode image signal, which is tomographic image information regarding tissues inside the subject, by performing, on the sound ray signal received from the transmission and reception circuit 42, correction of the attenuation due to the distance according to the depth of the reflection position of the ultrasound wave using a sound velocity value set by the probe controller 47 and then performing envelope detection processing.

The DSC 66 converts (raster-converts) the B-mode image signal generated by the signal processing section 65 into an image signal conforming to a normal television signal scanning method.

The image processing section 67 performs various types of necessary image processing such as gradation processing on the B-mode image signal input from the DSC 66 and then sends out the B-mode image signal to the probe side communication circuit 44. Hereinafter, the B-mode image signal that has been subjected to image processing by the image processing section 67 will be referred to as an ultrasound image.

The position information module 45 is used to detect the position of the ultrasound probe 4 to acquire position information, and for example, a module that detects an azimuthal angle of the ultrasound probe 4 with respect to the diagnostic apparatus 2 by using existing technologies such as Bluetooth low energy (BLE) 5.1 and ultra wideband (UWB) can be used.

In addition, the position information module 45 may detect the position of the ultrasound probe 4 by using a global positioning system (GPS) sensor or a wireless local area network (LAN) technology.

The probe side communication circuit 44 includes an antenna for transmitting and receiving radio waves, and modulates a carrier based on the ultrasound image generated by the image generation unit 43 and the position information of the ultrasound probe 4 acquired by the position information module 45 to generate a transmission signal representing the ultrasound image and the position information of the ultrasound probe 4, and demodulates transmission signals received from the portable terminal 5 and the diagnostic apparatus 2. As the modulation method of the carrier, for example, amplitude shift keying (ASK), phase shift keying (PSK), quadrature phase shift keying (QPSK), 16 quadrature amplitude modulation (16QAM), or the like is used.

The probe side communication circuit 44 supplies the transmission signal generated in this manner to the antenna and transmits radio waves from the antenna, thereby wirelessly transmitting the ultrasound image in association with the position information of the ultrasound probe 4 toward the terminal side communication circuit 51 of the portable terminal 5 and the diagnostic apparatus side communication circuit 21 of the diagnostic apparatus 2.

The notification unit 46 notifies the operator of the image acquisition apparatus G1 in a case in which the position information of the ultrasound probe 4 in the image acquisition apparatus G1 corresponds to position information designated from the diagnostic apparatus 2. The notification unit 46 can issue a notification by using at least one of sound, vibration, or light.

For example, in a case in which the ultrasound probe 4 has a probe side monitor (not shown), the notification unit 46 can issue a notification by displaying a message on the probe side monitor. In addition, in a case in which the ultrasound probe 4 has a speaker (not shown), the notification unit 46 can issue a notification through sound emitted via the speaker. Further, in a case in which the ultrasound probe 4 has a vibration generation device (not shown) that vibrates the ultrasound probe 4, the notification unit 46 can issue a notification by vibrating the ultrasound probe 4 through the vibration generation device.

The probe controller 47 controls each unit of the ultrasound probe 4 based on a control program or the like stored in advance.

Although the probe side processor 48 having the transmission and reception circuit 42, the image generation unit 43, the notification unit 46, and the probe controller 47 is configured with a central processing unit (CPU) and a control program for causing the CPU to perform various types of processing, the probe side processor 48 may be configured with a field programmable gate array (FPGA), a digital signal processor (DSP), an application specific integrated circuit (ASIC), a graphics processing unit (GPU), or other integrated circuits (ICs) or may be configured with a combination thereof.

In addition, the transmission and reception circuit 42, the image generation unit 43, the notification unit 46, and the probe controller 47 of the probe side processor 48 can also be configured by being partially or wholly integrated into one CPU or the like.

A battery (not shown) is incorporated into the ultrasound probe 4, and power is supplied from the battery to each unit of the ultrasound probe 4.

The terminal side communication circuit 51 of the portable terminal 5 includes an antenna for transmitting and receiving radio waves, and receives the transmission signal representing the ultrasound image, which is transmitted from the probe side communication circuit 44 of the ultrasound probe 4, via the antenna and demodulates the received transmission signal, for example, through the method such as ASK, PSK, QPSK, or 16QAM, to send out the ultrasound image to the display controller 52.

The display controller 52 performs predetermined processing on the ultrasound image sent out from the terminal side communication circuit 51 and displays the ultrasound image on the terminal side monitor 53, under the control of the terminal controller 54.

The terminal side monitor 53 is used to display the ultrasound image under the control of the display controller 52, and has, for example, a display device such as a liquid crystal display (LCD) or an organic electroluminescence (EL) display.

The terminal controller 54 controls each unit of the portable terminal 5 based on a control program or the like stored in advance.

The input device 55 is a device that is used for the user to perform an input operation, and includes, for example, a device such as a keyboard, a mouse, a track ball, a touch pad, and a touch sensor that is disposed by being overlaid on the terminal side monitor 53.

The terminal side processor 56 having the display controller 52 and the terminal controller 54 is configured with a CPU and a control program for causing the CPU to perform various types of processing, but the terminal side processor 56 may be configured with FPGA, DSP, ASIC, GPU, or other ICs or may be configured with a combination thereof.

In addition, the display controller 52 and the terminal controller 54 of the terminal side processor 56 can also be configured by being partially or wholly integrated into one CPU or the like.

A battery (not shown) is incorporated into the portable terminal 5, and power is supplied from the battery to each unit of the portable terminal 5.

The diagnostic apparatus side communication circuit 21 of the diagnostic apparatus 2 includes an antenna for transmitting and receiving radio waves, and receives the transmission signal representing the ultrasound image transmitted from the probe side communication circuit 44 of the ultrasound probe 4 and the position information of the ultrasound probe 4 in the image acquisition apparatus G1 via the antenna and demodulates the received transmission signal, for example, through the method such as ASK, PSK, QPSK, or 16QAM, to send out the ultrasound image to the display controller 22 and to send out the position information of the ultrasound probe 4 to the identification mark generation unit 23.

Similarly, the diagnostic apparatus side communication circuit 21 receives the transmission signal representing the ultrasound image and the position information of the ultrasound probe 4, which is transmitted from the probe side communication circuit 44 of the ultrasound probe 4 in each of the image acquisition apparatuses G2 to G4, via the antenna, and demodulates the received transmission signal to sequentially send out the ultrasound image to the display controller 22 and to sequentially send out the position information of the ultrasound probe 4 to the identification mark generation unit 23.

The identification mark generation unit 23 generates an identification mark corresponding to the position information of the ultrasound probe 4 in the image acquisition apparatus G1, which is sent out from the diagnostic apparatus side communication circuit 21. For example, the identification mark generation unit 23 can generate a mark representing a direction from the diagnostic apparatus 2 toward the ultrasound probe 4 of the image acquisition apparatus G1 as the identification mark based on the position information of the ultrasound probe 4.

Similarly, the identification mark generation unit 23 generates the identification mark corresponding to the position information of each of the ultrasound probes 4 in the image acquisition apparatuses G2 to G4, which is sent out from the diagnostic apparatus side communication circuit 21. For example, the identification mark generation unit 23 generates respective marks representing directions from the diagnostic apparatus 2 toward the ultrasound probes 4 of the image acquisition apparatuses G2 to G4 as the identification marks.

The display controller 22 performs predetermined processing on the ultrasound image sent out from the diagnostic apparatus side communication circuit 21 and the identification mark generated by the identification mark generation unit 23 and displays the ultrasound image and the identification mark on the diagnostic apparatus side monitor 3, under the control of the diagnostic apparatus controller 24.

Specifically, the display controller 22 displays a plurality of ultrasound images acquired by the image acquisition apparatuses G1 to G4 and a plurality of identification marks generated by the identification mark generation unit 23 and corresponding to the image acquisition apparatuses G1 to G4 on the diagnostic apparatus side monitor 3.

The diagnostic apparatus controller 24 controls each unit of the diagnostic apparatus 2 based on a control program or the like stored in advance.

The input device 25 is a device that is used for the user to perform an input operation, and includes, for example, a device such as a keyboard, a mouse, a track ball, a touch pad, and a touch sensor that is disposed by being overlaid on the diagnostic apparatus side monitor 3.

The diagnostic apparatus side processor 26 having the display controller 22, the identification mark generation unit 23, and the diagnostic apparatus controller 24 is configured with a CPU and a control program for causing the CPU to perform various types of processing, but the diagnostic apparatus side processor 26 may be configured with FPGA, DSP, ASIC, GPU, or other ICs or may be configured with a combination thereof.

In addition, the display controller 22, the identification mark generation unit 23, and the diagnostic apparatus controller 24 of the diagnostic apparatus side processor 26 can also be configured by being partially or wholly integrated into one CPU or the like.

The diagnostic apparatus side monitor 3 has, for example, a display device such as an LCD or an organic EL display, and displays the ultrasound image and the identification mark under the control of the display controller 22 of the diagnostic apparatus 2.

Figure 5:
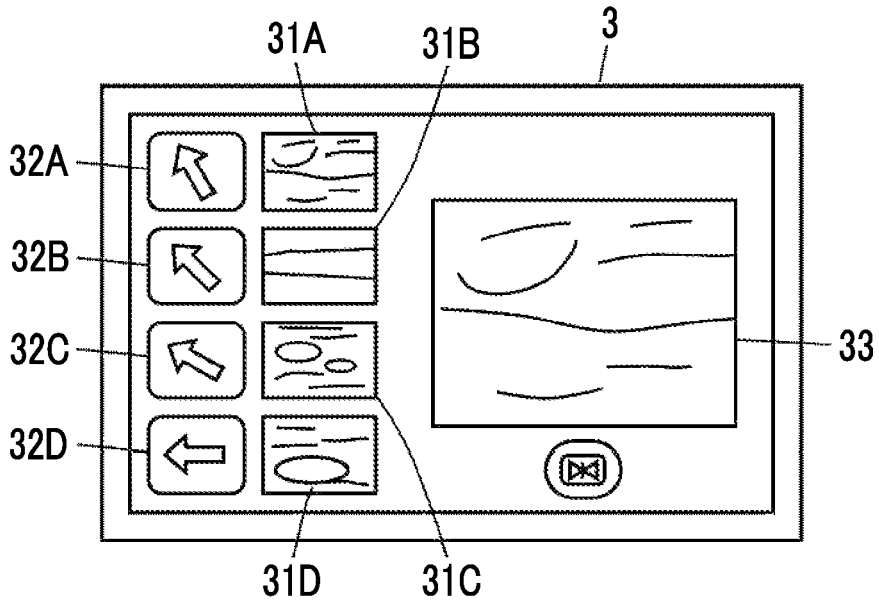
FIG. 5 is a diagram showing a display screen of a diagnostic apparatus side monitor in Embodiment 1 of the present invention.

FIG. 5 shows an example of a display screen on the diagnostic apparatus side monitor 3. A plurality of ultrasound images 31A to 31D acquired by the image acquisition apparatuses G1 to G4 are displayed on one screen of the diagnostic apparatus side monitor 3. These ultrasound images 31A to 31D are ultrasound images of the subjects P1 to P4 that are captured using the respective ultrasound probes 4 of the image acquisition apparatuses G1 to G4.

In addition, on the diagnostic apparatus side monitor 3, a plurality of identification marks 32A to 32D are displayed in the vicinity of the ultrasound images 31A to 31D to correspond to the plurality of ultrasound images 31A to 31D. These identification marks 32A to 32D represent arrows indicating directions from the diagnostic apparatus 2 toward the respective ultrasound probes 4 of the image acquisition apparatuses G1 to G4.

In a case in which any of the plurality of ultrasound images 31A to 31D is designated by the user, an enlarged image 33 obtained by enlarging the designated ultrasound image is displayed on the screen of the diagnostic apparatus side monitor 3.

Figure 6:
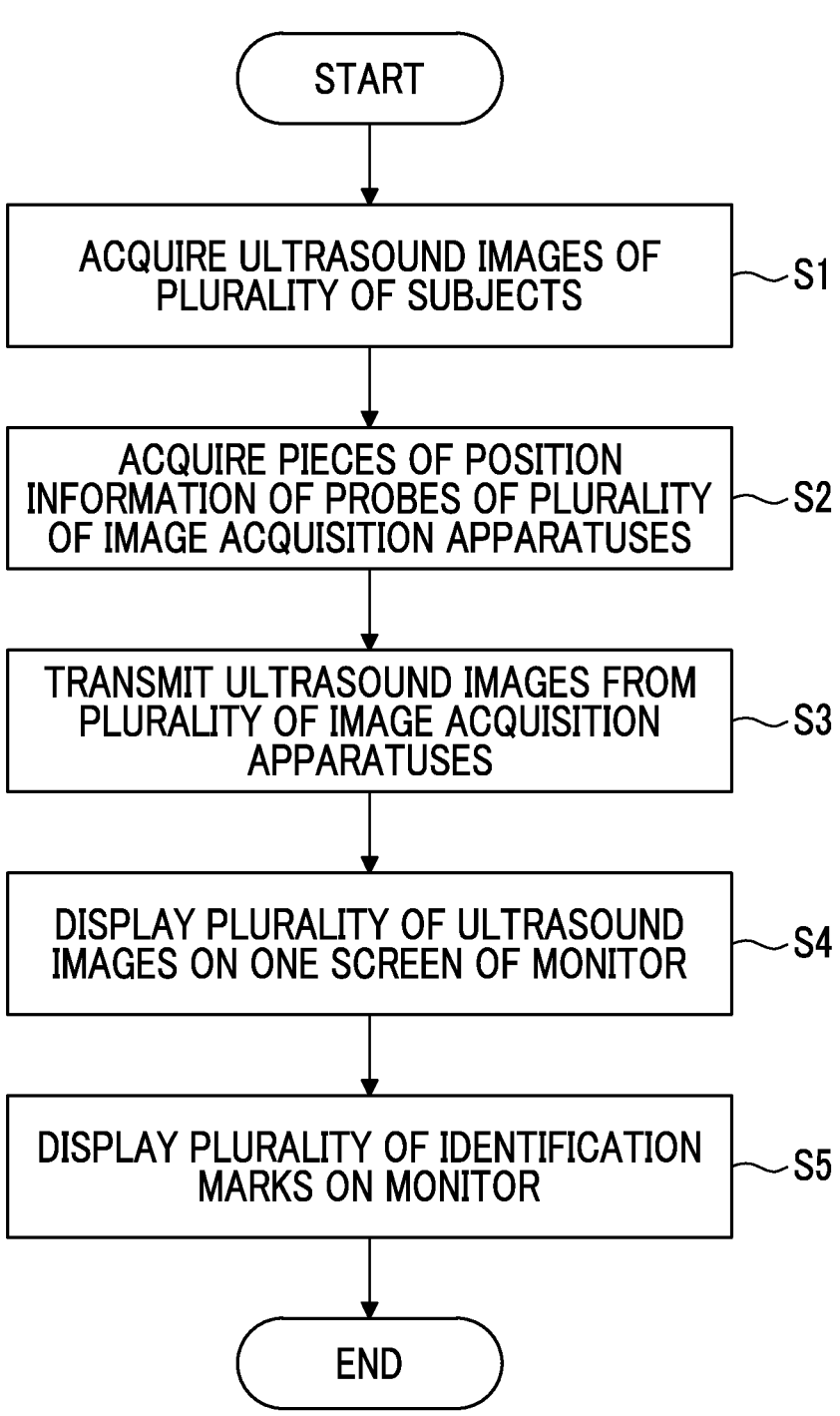
FIG. 6 is a flowchart showing an operation of the ultrasound diagnostic system according to Embodiment 1 of the present invention.

Next, an operation of the ultrasound diagnostic system according to Embodiment 1 will be described with reference to a flowchart shown in FIG. 6.

First, in step S1, the plurality of subjects P1 to P4 are subjected to ultrasound imaging using the ultrasound probes 4 of the plurality of image acquisition apparatuses G1 to G4, and the ultrasound images of the subjects P1 to P4 are acquired, respectively.

In this case, under the control of the probe controller 47, transmission and reception of ultrasound waves are started from the plurality of transducers of the transducer array 41 in accordance with the drive signal from the pulsar 61 of the transmission and reception circuit 42, the ultrasound echoes from the internal tissues of the subject are received by the plurality of transducers of the transducer array 41, and a reception signal which is an analog signal is output to the amplification section 62 and amplified and is subjected to AD conversion by the AD conversion section 63, thereby acquiring reception data.

The reception focus processing is performed on this reception data by the beam former 64, the sound ray signal generated through this is sent out to the image generation unit 43, and the ultrasound image representing tomographic image information of the subject is generated by the image generation unit 43. In this case, the sound ray signal is subjected to the attenuation correction corresponding to the depth of the reflection position of the ultrasound wave and the envelope detection processing by the signal processing section 65 of the image generation unit 43, is converted into the image signal conforming to the normal television signal scanning method by the DSC 66, and is subjected to various types of necessary image processing, such as gradation processing, by the image processing section 67.

The ultrasound image captured by the ultrasound probe 4 in this manner is transmitted from the probe side communication circuit 44 of the ultrasound probe 4 to the terminal side communication circuit 51 of the portable terminal 5 within the same image acquisition apparatus, and is displayed on the terminal side monitor 53 via the display controller 52. As a result, the operators who operate the image acquisition apparatuses G1 to G4, such as ultrasound technicians or nurses, can acquire the ultrasound images while checking the ultrasound images of the corresponding subjects P1 to P4.

Next, in step S2, the pieces of position information of the ultrasound probes 4 in a case in which the ultrasound images are acquired by the position information modules 45 of the ultrasound probes 4 of the plurality of image acquisition apparatuses G1 to G4 are acquired, respectively. For example, the position information module 45 can acquire the position information including the azimuthal angle of the ultrasound probe 4 with respect to the diagnostic apparatus 2 by using BLE 5.1 or UWB.

Further, in step S3, the ultrasound images of the subjects P1 to P4 acquired by the plurality of image acquisition apparatuses G1 to G4 are wirelessly transmitted from the ultrasound probes 4 of the image acquisition apparatuses G1 to G4 to the diagnostic apparatus 2, respectively. In this case, in the ultrasound probe 4 of each of the image acquisition apparatuses G1 to G4, the ultrasound image generated by the image generation unit 43 is wirelessly transmitted from the probe side communication circuit 44 toward the diagnostic apparatus 2 in a state of being associated with the position information of the ultrasound probe 4 acquired by the position information module 45.

In subsequent step S4, the ultrasound images respectively wirelessly transmitted from the ultrasound probes 4 of the image acquisition apparatuses G1 to G4 to the diagnostic apparatus 2 are received by the diagnostic apparatus side communication circuit 21 of the diagnostic apparatus 2, and are displayed on one screen of the diagnostic apparatus side monitor 3 via the display controller 22.

Further, the pieces of position information of the ultrasound probe 4 associated with the ultrasound images respectively wirelessly transmitted from the ultrasound probes 4 of the image acquisition apparatuses G1 to G4 are sent out from the diagnostic apparatus side communication circuit 21 to the identification mark generation unit 23, and the identification marks corresponding to the pieces of position information of the ultrasound probes 4 of the image acquisition apparatuses G1 to G4 are generated by the identification mark generation unit 23, respectively.

For example, the identification mark generation unit 23 generates the respective marks representing the directions from the diagnostic apparatus 2 toward the ultrasound probes 4 of the image acquisition apparatuses G1 to G4 as the identification marks based on the pieces of position information including the azimuthal angles of the ultrasound probes 4 of the image acquisition apparatuses G1 to G4 with respect to the diagnostic apparatus 2.

Then, in step S5, a plurality of identification marks corresponding to the ultrasound probes 4 of the image acquisition apparatuses G1 to G4, which are generated by the identification mark generation unit 23, are displayed in the vicinity of the plurality of ultrasound images corresponding to the image acquisition apparatuses G1 to G4, which are displayed on the diagnostic apparatus side monitor 3.

As a result, as shown in FIG. 5, the plurality of ultrasound images 31A to 31D acquired by the plurality of image acquisition apparatuses G1 to G4 and the plurality of identification marks 32A to 32D corresponding to the plurality of ultrasound images 31A to 31D are displayed on one screen of the diagnostic apparatus side monitor 3.

Therefore, even in a case in which the user who observes the diagnostic apparatus side monitor 3 and operates the diagnostic apparatus 2, such as a doctor, is located away from the plurality of subjects P1 to P4 and the image acquisition apparatuses G1 to G4, the user can easily and accurately understand which of the plurality of ultrasound images 31A to 31D corresponds to the ultrasound image obtained by capturing which of the subjects P1 to P4 by checking respective directions indicated by the identification marks 32A to 32D, which are displayed in the vicinity of the plurality of ultrasound images 31A to 31D.

It should be noted that there is no need to perform all the acquisition of the ultrasound images of the plurality of subjects P1 to P4 in step S1, the acquisition of the pieces of position information of the ultrasound probes 4 of the plurality of image acquisition apparatuses G1 to G4 in step S2, and the wireless transmission of the ultrasound images from the plurality of image acquisition apparatuses G1 to G4 to the diagnostic apparatus 2 in step S3 at the same timing in the plurality of image acquisition apparatuses G1 to G4, and the ultrasound image and the position information of the ultrasound probe 4 acquired in each of the image acquisition apparatuses G1 to G4 need only be wirelessly transmitted to the diagnostic apparatus 2 as appropriate.

In a case in which any of the ultrasound images 31A to 31D of the subjects P1 to P4 displayed on the diagnostic apparatus side monitor 3 is designated by the user who operates the diagnostic apparatus 2, such as a doctor, the designated ultrasound image is enlarged and displayed on the diagnostic apparatus side monitor 3 as the enlarged image 33, and a notification is made to the operator of the image acquisition apparatuses G1 to G4 by the notification unit 46 of the ultrasound probe 4 of the image acquisition apparatuses G1 to G4 that has acquired the designated ultrasound image.

That is, in a case in which any of the ultrasound images 31A to 31D is designated by the user, a command to issue a notification is wirelessly transmitted from the diagnostic apparatus side communication circuit 21 to the ultrasound probe 4 having the position information associated with the designated ultrasound image, under the control of the diagnostic apparatus controller 24, and the notification unit 46 is operated by the probe controller 47 of the ultrasound probe 4 that has received the command via the probe side communication circuit 44.

The notification unit 46 can notify the operators of the image acquisition apparatuses G1 to G4 having the ultrasound probes 4 by using at least one of sound, vibration, or light.

As a result, the operator who has received the notification, such as an ultrasound technician or a nurse, can recognize that diagnosis by the user such as a doctor is made for the ultrasound image obtained by capturing the subject for which the operator is responsible among the plurality of subjects P1 to P4. Therefore, for example, it is also possible to acquire a new ultrasound image of the subject in response to an instruction to further capture an ultrasound image from the user who operates the diagnostic apparatus 2.

As described above, with the ultrasound diagnostic system according to Embodiment 1, the ultrasound images of the plurality of subjects P1 to P4 can be displayed on one screen of the diagnostic apparatus side monitor 3, and proper diagnoses can be performed on the plurality of subjects P1 to P4 at once by using the single diagnostic apparatus 2.

In Embodiment 1 described above, the position information modules 45 of the ultrasound probes 4 in the image acquisition apparatuses G1 to G4 use BLE 5.1, UWB, or the like to acquire the pieces of position information including the azimuthal angles of the ultrasound probes 4 with respect to the diagnostic apparatus 2, but the present invention is not limited to this. For example, the position information module 45 can detect the position of the ultrasound probe 4 using a GPS sensor or a wireless LAN technology, and the identification mark generation unit 23 of the diagnostic apparatus 2 can also calculate the azimuthal angle of the ultrasound probe 4 with respect to the diagnostic apparatus 2 based on the position of the diagnostic apparatus 2 and the position of the ultrasound probe 4. Even in this manner, the respective marks representing directions from the diagnostic apparatus 2 toward the ultrasound probes 4 of the image acquisition apparatuses G1 to G4 can be generated as the identification marks.

In Embodiment 1 described above, although the ultrasound probes 4 of the plurality of image acquisition apparatuses G1 to G4 are each wirelessly connected to the diagnostic apparatus 2, a similar configuration may also be employed such that the portable terminals 5 of the plurality of image acquisition apparatuses G1 to G4 are each wirelessly connected to the diagnostic apparatus 2.

In this case, the ultrasound images of the subjects P1 to P4 captured by the ultrasound probes 4 and the pieces of position information of the ultrasound probes 4 are wirelessly transmitted from the probe side communication circuits 44 of the ultrasound probes 4 to the terminal side communication circuits 51 of the portable terminals 5, and then, are wirelessly transmitted from the terminal side communication circuits 51 of the portable terminals 5 to the diagnostic apparatus side communication circuit 21 of the diagnostic apparatus 2.

The plurality of image acquisition apparatuses G1 to G4 are not limited to four as shown in FIG. 1, and two or more image acquisition apparatuses need only be wirelessly connected to the diagnostic apparatus 2.

Further, in each of the image acquisition apparatuses G1 to G4, the ultrasound probe 4 and the portable terminal 5 may be connected to each other in a wired manner instead of being connected to each other in a wireless manner.

In a case in which the number of subjects P1 to P4 that require diagnosis is greater than the number of image acquisition apparatuses G1 to G4, it is also possible to accumulate a plurality of ultrasound images acquired from a plurality of subjects on a single image acquisition apparatus for each subject and then, wirelessly transmit the accumulated ultrasound images to the diagnostic apparatus 2 in bulk.

Embodiment 2

In Embodiment 1 described above, the respective marks representing the directions from the diagnostic apparatus 2 toward the ultrasound probes 4 of the image acquisition apparatuses G1 to G4 are generated as the identification marks by the identification mark generation unit 23 of the diagnostic apparatus 2, and are displayed on the diagnostic apparatus side monitor 3, but the present invention is not limited to this.

Figure 7:
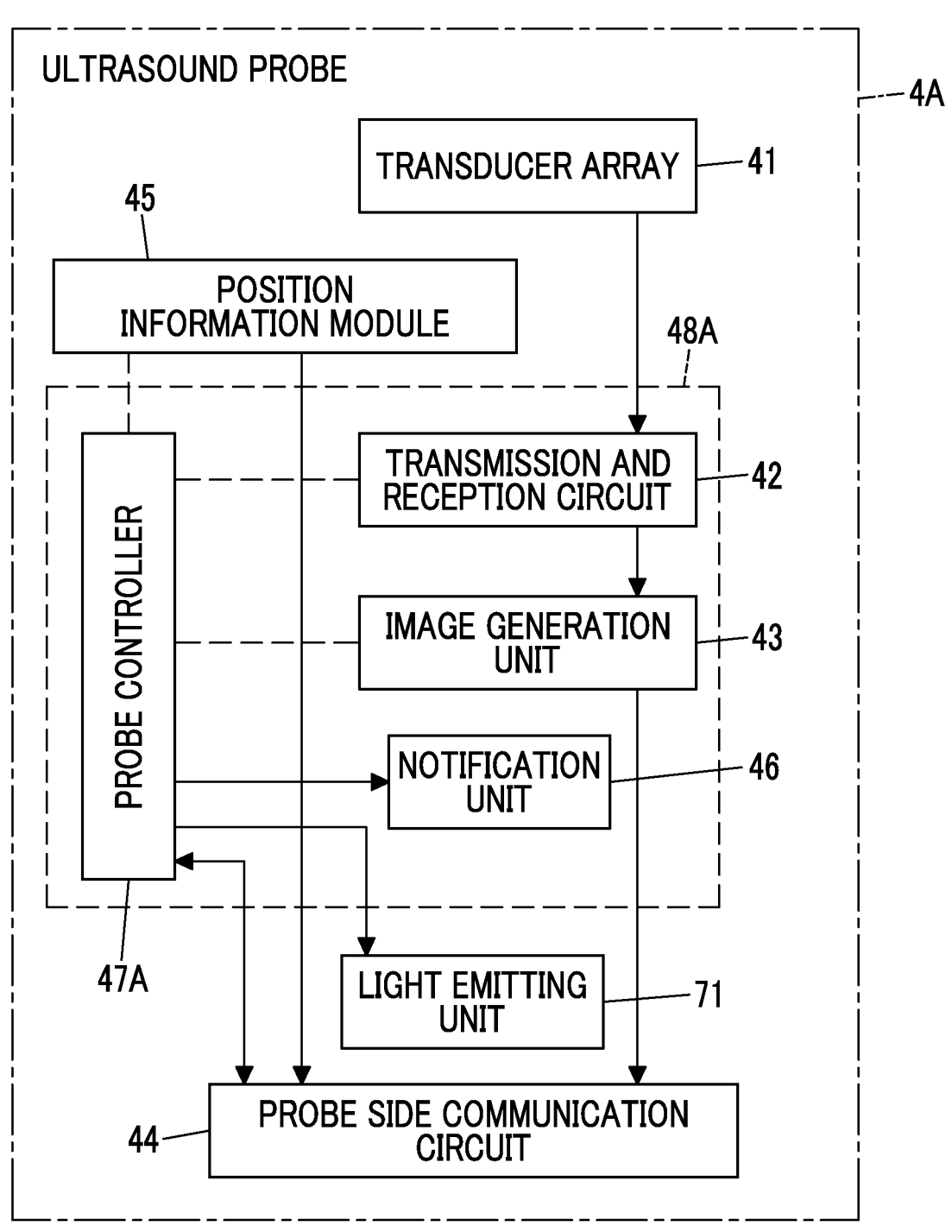
FIG. 7 is a block diagram showing an internal configuration of an ultrasound probe of each image acquisition apparatus in Embodiment 2 of the present invention.

FIG. 7 shows an internal configuration of an ultrasound probe 4A of each image acquisition apparatus in an ultrasound diagnostic system according to Embodiment 2. The ultrasound probe 4A is obtained by newly adding a light emitting unit 71 and using a probe controller 47A and a probe side processor 48A instead of the probe controller 47 and the probe side processor 48, with respect to the ultrasound probe 4 shown in FIG. 2, and other configurations are the same as those of the ultrasound probe 4.

The light emitting unit 71 is connected to the probe controller 47A and selectively emits rays of light of a plurality of colors under the control of the probe controller 47A. The light emitting units 71 in the ultrasound probes 4A of the plurality of image acquisition apparatuses G1 to G4 are configured to emit rays of light of different colors from each other.

Figure 8:
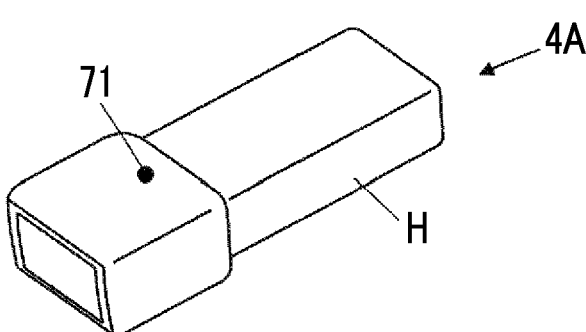
FIG. 8 is a perspective view showing an appearance of the ultrasound probe of each image acquisition apparatus in Embodiment 2 of the present invention.

Such a light emitting unit 71 is formed of, for example, a light emitting diode (LED) or an organic light emitting diode (OLED), and is disposed on an outer surface of a housing H of the ultrasound probe 4A or disposed inside the housing H having light-transmitting property, which makes it possible to recognize the light emitted by the light emitting unit 71 from the outside of the ultrasound probe 4A, as shown in FIG. 8.

The identification mark generation unit 23 of the diagnostic apparatus 2 generates an identification mark having a color corresponding to the light emitted from the light emitting unit 71 of each of the ultrasound probes 4A, for example, the same color as that of the light emitted from the light emitting unit 71, in correspondence with the pieces of position information of the ultrasound probes 4A of the image acquisition apparatuses G1 to G4. This identification mark is displayed on the diagnostic apparatus side monitor 3 in the vicinity of the plurality of ultrasound images 31A to 31D acquired by the image acquisition apparatuses G1 to G4.

It should be noted that the term "the color corresponding to the light emitted from the light emitting unit 71" includes not only the same color as that of the light emitted from the light emitting unit 71 but also a color that has a spectrum similar to the spectrum of the light emitted from the light emitting unit 71 and that can be perceived by the user as being of the same hue.

Figure 9:
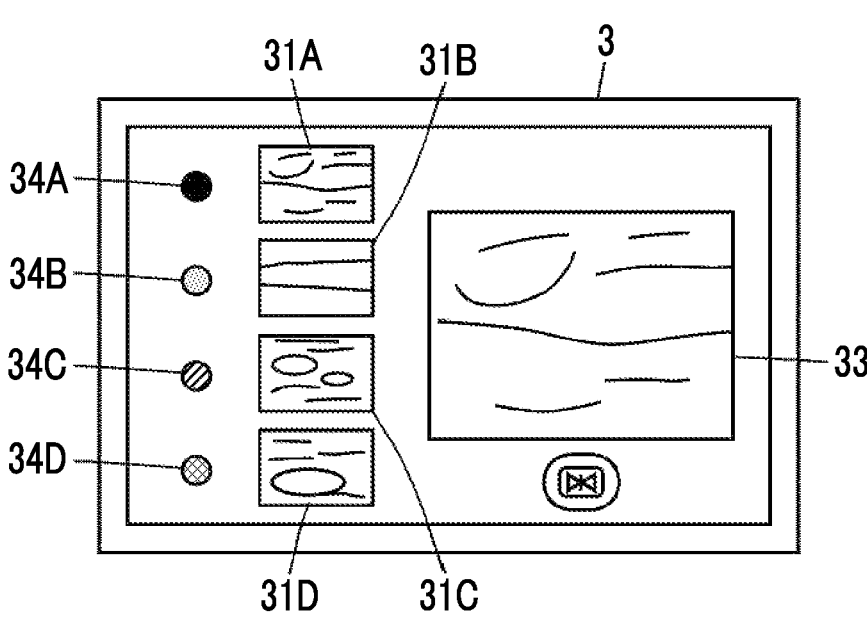
FIG. 9 is a diagram showing a display screen of a diagnostic apparatus side monitor in Embodiment 2 of the present invention.

FIG. 9 shows an example of the display screen of the diagnostic apparatus side monitor 3 in Embodiment 2. Similarly to Embodiment 1, the plurality of ultrasound images 31A to 31D acquired by the image acquisition apparatuses G1 to G4 are displayed on one screen of the diagnostic apparatus side monitor 3, and a plurality of identification marks 34A to 34D are displayed in the vicinity of the ultrasound images 31A to 31D to correspond to the ultrasound images 31A to 31D. These identification marks 34A to 34D have different colors from each other and have colors corresponding to the rays of light emitted from the light emitting units 71 of the ultrasound probes 4A of the image acquisition apparatuses G1 to G4 corresponding to the ultrasound images 31A to 31D displayed in the vicinity thereof, for example, the same colors as those of the rays of light emitted from the light emitting units 71, respectively.

As described above, the rays of light emitted from the light emitting units 71 of the ultrasound probes 4A of the image acquisition apparatuses G1 to G4 that have acquired the ultrasound images 31A to 31D of the plurality of subjects P1 to P4 and the identification marks 34A to 34D located in the vicinity of the ultrasound images 31A to 31D displayed on the diagnostic apparatus side monitor 3 have colors corresponding to each other, so that it is possible to easily and accurately associate the ultrasound images 31A to 31D with the ultrasound probes 4A of the image acquisition apparatuses G1 to G4 that have acquired the ultrasound images 31A to 31D.

Therefore, even in a case in which the user who operates the diagnostic apparatus 2 is located away from the plurality of subjects P1 to P4 and the image acquisition apparatuses G1 to G4, it is possible to easily and accurately specify the subject to be a diagnostic target by conveying the color of the identification marks 34A to 34D located in the vicinity of one ultrasound image to be diagnosed among the ultrasound images 31A to 31D, to the operator who operates the image acquisition apparatuses G1 to G4.

In a case in which the ultrasound images associated with the pieces of position information of the ultrasound probes 4A of the image acquisition apparatuses G1 to G4 are wirelessly transmitted from the probe side communication circuits 44 of the ultrasound probes 4A to the diagnostic apparatus 2, color information indicating the colors of the rays of light emitted from the light emitting units 71 of the ultrasound probes 4A can also be wirelessly transmitted to the diagnostic apparatus 2 together with the pieces of position information and the ultrasound images. In this manner, the identification mark generation unit 23 can generate the identification marks 34A to 34D of the colors corresponding to the colors of the rays of light emitted from the light emitting units 71 of the ultrasound probes 4A based on the color information wirelessly transmitted from the ultrasound probes 4A of the image acquisition apparatuses G1 to G4.

Further, on the display screen of the diagnostic apparatus side monitor 3 shown in FIG. 9, the circular identification marks 34A to 34D are displayed in the vicinity of the ultrasound images 31A to 31D, but the present invention is not limited to this, and a frame-like shaped identification marks respectively surrounding the ultrasound images 31A to 31D can also be used.

Embodiment 3

Figure 10:
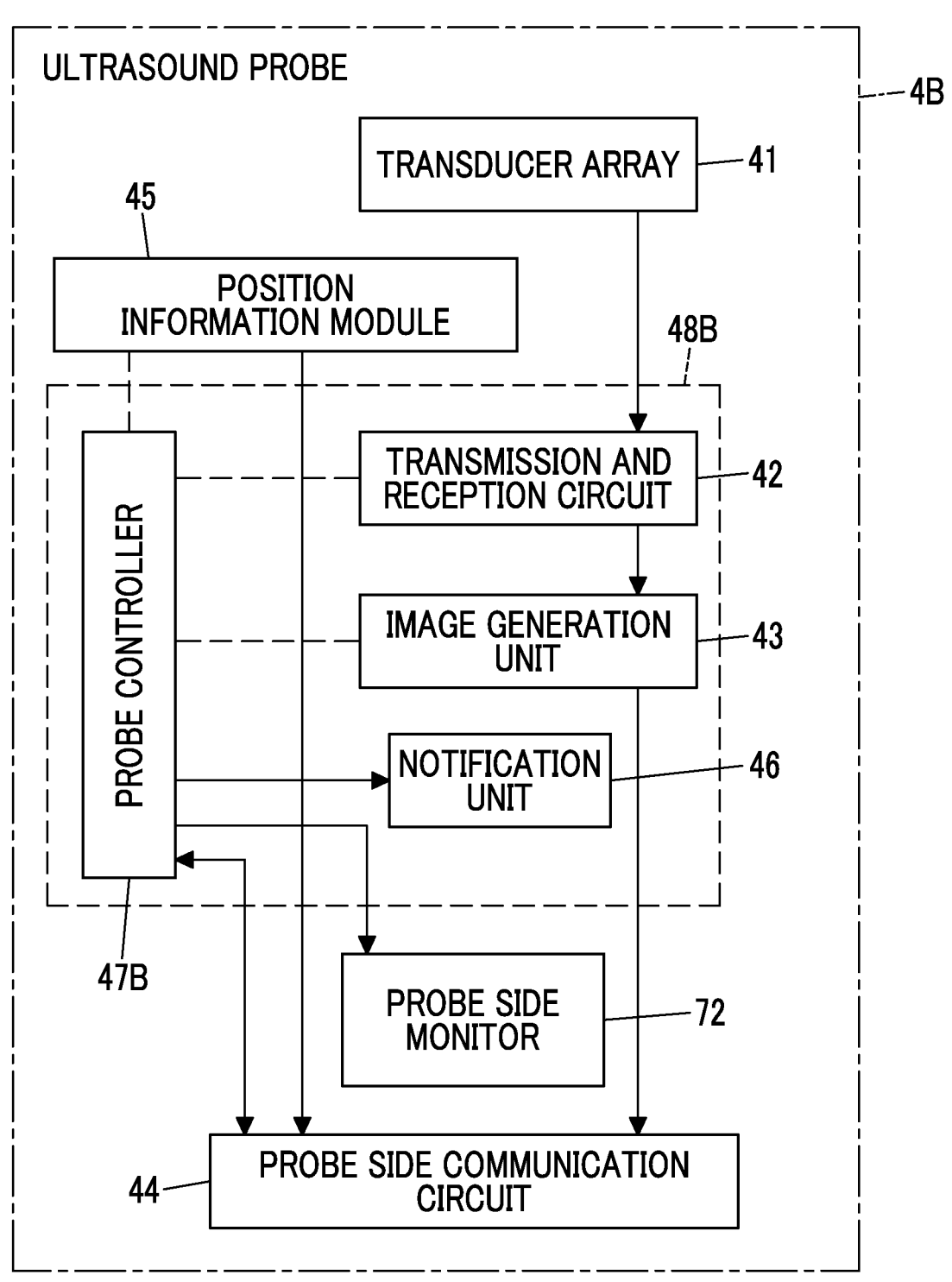
FIG. 10 is a block diagram showing an internal configuration of an ultrasound probe of each image acquisition apparatus in Embodiment 3 of the present invention.

FIG. 10 shows an internal configuration of an ultrasound probe 4B of each image acquisition apparatus in an ultrasound diagnostic system according to Embodiment 3. The ultrasound probe 4B is obtained by newly adding a probe side monitor 72 and using a probe controller 47B and a probe side processor 48B instead of the probe controller 47 and the probe side processor 48, with respect to the ultrasound probe 4 shown in FIG. 2, and other configurations are the same as those of the ultrasound probe 4.

The probe side monitor 72 is connected to the probe controller 47B and displays a predetermined probe side mark consisting of a sign, a number, a symbol, a figure, or the like under the control of the probe controller 47B. The probe side monitors 72 in the ultrasound probes 4B of the plurality of image acquisition apparatuses G1 to G4 are configured to display probe side marks having different shapes from each other.

Figure 11:
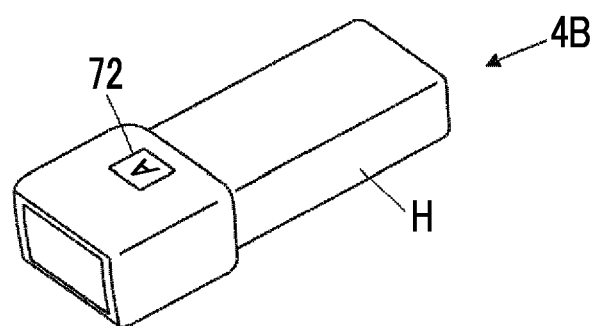
FIG. 11 is a perspective view showing an appearance of the ultrasound probe of each image acquisition apparatus in Embodiment 3 of the present invention.

The probe side monitor 72 has, for example, a display device such as an LCD or an organic EL display and is disposed on the outer surface of the housing H of the ultrasound probe 4B as shown in FIG. 11.

The identification mark generation unit 23 of the diagnostic apparatus 2 generates an identification mark having a shape corresponding to the probe side mark displayed on the probe side monitor 72 of each of the ultrasound probes 4B, for example, the same shape as that of the probe side mark, in correspondence with the pieces of position information of the ultrasound probes 4B of the image acquisition apparatuses G1 to G4. This identification mark is displayed on the diagnostic apparatus side monitor 3 in the vicinity of the plurality of ultrasound images 31A to 31D acquired by the image acquisition apparatuses G1 to G4.

It should be noted that the term "the shape corresponding to the probe side mark" includes not only the same shape as that of the probe side mark but also a shape that is similar to the probe side mark and that allows the user to have a common concept with the probe side mark. For example, a mark representing a single alphabet in uppercase and a mark representing the alphabet in lowercase have shapes corresponding to each other.

16

Figure 12:
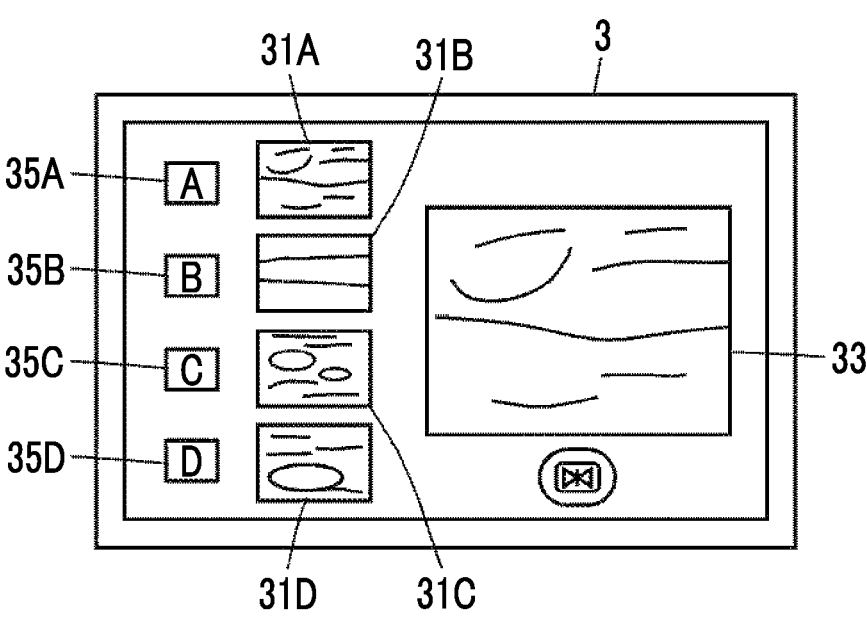
FIG. 12 is a diagram showing a display screen of a diagnostic apparatus side monitor in Embodiment 3 of the present invention.

An example of the display screen of the diagnostic apparatus side monitor 3 in Embodiment 3 is shown in FIG. 12. Similarly to Embodiment 1, the plurality of ultrasound images 31A to 31D acquired by the image acquisition apparatuses G1 to G4 are displayed on one screen of the diagnostic apparatus side monitor 3, and a plurality of identification marks 35A to 35D are displayed in the vicinity of the ultrasound images 31A to 31D to correspond to the ultrasound images 31A to 31D. These identification marks 35A to 35D have different shapes from each other and have shapes corresponding to the probe side marks displayed on the probe side monitors 72 of the ultrasound probes 4B of the image acquisition apparatuses G1 to G4 corresponding to the ultrasound images 31A to 31D displayed in the vicinity thereof, respectively. The identification marks 35A to 35D shown in FIG. 12 are formed of the uppercase alphabets, that is, "A", "B", "C", and "D".

As described above, the probe side marks displayed on the probe side monitors 72 of the ultrasound probes 4B of the image acquisition apparatuses G1 to G4 that have acquired the ultrasound images 31A to 31D of the plurality of subjects P1 to P4 and the identification marks 35A to 35D located in the vicinity of the ultrasound images 31A to 31D displayed on the diagnostic apparatus side monitor 3 have shapes corresponding to each other, so that it is possible to easily and accurately associate the ultrasound images 31A to 31D with the ultrasound probes 4B of the image acquisition apparatuses G1 to G4 that have acquired the ultrasound images 31A to 31D.

Therefore, even in a case in which the user who operates the diagnostic apparatus 2 is located away from the plurality of subjects P1 to P4 and the image acquisition apparatuses G1 to G4, it is possible to easily and accurately specify the subject to be a diagnostic target by conveying the shape of the identification marks 35A to 35D located in the vicinity of one ultrasound image to be diagnosed among the ultrasound images 31A to 31D, to the operator who operates the image acquisition apparatuses G1 to G4.

In a case in which the ultrasound images associated with the pieces of position information of the ultrasound probes 4B of the image acquisition apparatuses G1 to G4 are wirelessly transmitted from the probe side communication circuits 44 of the ultrasound probes 4B to the diagnostic apparatus 2, mark information indicating the probe side marks displayed on the probe side monitors 72 of the ultrasound probes 4B can also be wirelessly transmitted to the diagnostic apparatus 2 together with the pieces of position information and the ultrasound images. In this manner, the identification mark generation unit 23 can generate the identification marks 35A to 35D of the shapes corresponding to the probe side marks displayed on the probe side monitors 72 of the ultrasound probes 4B based on the mark information wirelessly transmitted from the ultrasound probes 4B of the image acquisition apparatuses G1 to G4.

EXPLANATION OF REFERENCES

2: diagnostic apparatus
3: diagnostic apparatus side monitor
4, 4A, 4B: ultrasound probe
5: portable terminal
21: diagnostic apparatus side communication circuit
22, 52: display controller
23: identification mark generation unit
24: diagnostic apparatus controller
25, 55: input device

17

18

26: diagnostic apparatus side processor
31A to 31D: ultrasound image
32A to 32D, 34A to 34D, 35A to 35D: identification mark
33: enlarged image
41: transducer array
42: transmission and reception circuit
43: image generation unit
44: probe side communication circuit
45: position information module
46: notification unit
47, 47A, 47B: probe controller
48, 48A, 48B: probe side processor
51: terminal side communication circuit
53: terminal side monitor
54: terminal controller
56: terminal side processor
61: pulsar
62: amplification section
63: AD conversion section
64: beam former
65: signal processing section
66: DSC
67: image processing section
71: light emitting unit
72: probe side monitor
P1 to P4: subject
G1 to G4: image acquisition apparatus
H: housing

What is claimed is:

1. An ultrasound diagnostic system comprising:
a plurality of image acquisition apparatuses disposed in a vicinity of a plurality of subjects in correspondence with the plurality of subjects, each having an ultrasound probe and a portable terminal that displays an ultrasound image of the corresponding subject acquired by using the ultrasound probe;
a diagnostic apparatus wirelessly connected to the plurality of image acquisition apparatuses; and
a diagnostic apparatus side monitor connected to the diagnostic apparatus,
wherein the diagnostic apparatus and the diagnostic apparatus side monitor are in a location different from the plurality of image acquisition apparatuses,
the ultrasound probes of the plurality of image acquisition apparatuses each include a position information acquisition module that acquires position information of the ultrasound probe,
the plurality of image acquisition apparatuses each wirelessly transmit the ultrasound image acquired by using the ultrasound probe to the diagnostic apparatus in association with the position information of the ultrasound probe acquired by the position information acquisition module,
the diagnostic apparatus displays ultrasound images of the plurality of subjects acquired by the plurality of image acquisition apparatuses together on one screen of the diagnostic apparatus side monitor,
the diagnostic apparatus displays a plurality of identification marks corresponding to a plurality of pieces of the position information associated with the ultrasound images of the plurality of subjects together on the one screen of the diagnostic apparatus side monitor in correspondence with the ultrasound images of the plurality of subjects, and
the diagnostic apparatus performs diagnoses on the plurality of subjects at once based on the ultrasound images of the plurality of subjects displayed at once on the one screen of the diagnostic apparatus side monitor.

2. The ultrasound diagnostic system according to claim 1, wherein the diagnostic apparatus has a diagnostic apparatus side processor that generates the plurality of identification marks.

3. The ultrasound diagnostic system according to claim 1, wherein the position information acquisition module is an azimuthal angle detection module that detects an azimuthal angle of the ultrasound probe with respect to the diagnostic apparatus as the position information.

4. The ultrasound diagnostic system according to claim 3, wherein the identification mark is a mark representing a direction from the diagnostic apparatus toward the ultrasound probe based on the azimuthal angle detected as the position information.

5. The ultrasound diagnostic system according to claim 2, wherein the position information acquisition module is an azimuthal angle detection module that detects an azimuthal angle of the ultrasound probe with respect to the diagnostic apparatus as the position information.

6. The ultrasound diagnostic system according to claim 5, wherein the identification mark is a mark representing a direction from the diagnostic apparatus toward the ultrasound probe based on the azimuthal angle detected as the position information.

7. The ultrasound diagnostic system according to claim 1, wherein the ultrasound probe of each respective image acquisition apparatus of the plurality of image acquisition apparatuses has a light emitting unit that selectively emits rays of light of a plurality of colors, and the identification mark has a color corresponding to the color of the light emitted from the light emitting unit.

8. The ultrasound diagnostic system according to claim 2, wherein the ultrasound probe of each respective image acquisition apparatus of the plurality of image acquisition apparatuses has a light emitting unit that selectively emits rays of light of a plurality of colors, and the identification mark has a color corresponding to the color of the light emitted from the light emitting unit.

9. The ultrasound diagnostic system according to claim 1, wherein the ultrasound probe of each respective image acquisition apparatus of the plurality of image acquisition apparatuses has a probe side monitor that displays a probe side mark, and the identification mark has a shape corresponding to the probe side mark.

10. The ultrasound diagnostic system according to claim 2, wherein the ultrasound probe of each respective image acquisition apparatus of the plurality of image acquisition apparatuses has a probe side monitor that displays a probe side mark, and the identification mark has a shape corresponding to the probe side mark.

11. The ultrasound diagnostic system according to claim 1, wherein each respective image acquisition apparatus of the plurality of image acquisition apparatuses has a processor provided in at least one of the ultrasound probe or the portable terminal, and in a case in which any of the ultrasound images of the plurality of subjects displayed on the diagnostic apparatus side monitor is designated by a user, a notification is made by the processor of the respective image acquisition apparatus having the ultrasound probe corresponding to the position information associated with the designated ultrasound image.

12. The ultrasound diagnostic system according to claim 4, wherein each respective image acquisition apparatus of the plurality of image acquisition apparatuses has a processor provided in at least one of the ultrasound probe or the portable terminal, and in a case in which any of the ultrasound images of the plurality of subjects displayed on the diagnostic apparatus side monitor is designated by a user, a notification is made by the processor of the respective image acquisition apparatus having the ultrasound probe corresponding to the position information associated with the designated ultrasound image.

13. The ultrasound diagnostic system according to claim 7, wherein each respective image acquisition apparatus of the plurality of image acquisition apparatuses has a processor provided in at least one of the ultrasound probe or the portable terminal, and in a case in which any of the ultrasound images of the plurality of subjects displayed on the diagnostic apparatus side monitor is designated by a user, a notification is made by the processor of the respective image acquisition apparatus having the ultrasound probe corresponding to the position information associated with the designated ultrasound image.

14. The ultrasound diagnostic system according to claim 9, wherein each respective image acquisition apparatus of the plurality of image acquisition apparatuses has a processor provided in at least one of the ultrasound probe or the portable terminal, and in a case in which any of the ultrasound images of the plurality of subjects displayed on the diagnostic apparatus side monitor is designated by a user, a notification is made by the processor of the respective image acquisition apparatus having the ultrasound probe corresponding to the position information associated with the designated ultrasound image.

15. The ultrasound diagnostic system according to claim 11, wherein the processor issues the notification by using at least one of sound, vibration, or light.

16. The ultrasound diagnostic system according to claim 12, wherein the processor issues the notification by using at least one of sound, vibration, or light.

17. The ultrasound diagnostic system according to claim 13, wherein the processor issues the notification by using at least one of sound, vibration, or light.

18. The ultrasound diagnostic system according to claim 1, wherein the ultrasound probe of each respective image acquisition apparatus of the plurality of image acquisition apparatuses is wirelessly connected to the diagnostic apparatus.

19. The ultrasound diagnostic system according to claim 1, wherein the portable terminal of each respective image acquisition apparatus of the plurality of image acquisition apparatuses is wirelessly connected to the diagnostic apparatus.

20. A control method of an ultrasound diagnostic system, comprising:

acquiring, in a plurality of image acquisition apparatuses disposed in a vicinity of a plurality of subjects in correspondence with the plurality of subjects, each having an ultrasound probe and a portable terminal that displays an ultrasound image of the corresponding subject acquired by using the ultrasound probe, position information of the ultrasound probe;

wirelessly transmitting the ultrasound image acquired by using the ultrasound probe in the plurality of image acquisition apparatuses to a diagnostic apparatus in association with the position information of the ultrasound probe;

displaying ultrasound images of the plurality of subjects acquired by the plurality of image acquisition apparatuses together on one screen of a diagnostic apparatus side monitor, the diagnostic apparatus and the diagnostic apparatus side monitor being in a location different from the plurality of image acquisition apparatuses;

displaying a plurality of identification marks corresponding to a plurality of pieces of the position information associated with the ultrasound images of the plurality of subjects together on the one screen of the diagnostic apparatus side monitor in correspondence with the ultrasound images of the plurality of subjects; and performing diagnoses on the plurality of subjects at once based on the ultrasound images of the plurality of subjects displayed at once on the one screen of the diagnostic apparatus side monitor.

* * * * *